(12) United States Patent
Byrnes et al.

(10) Patent No.: US 10,772,409 B2
(45) Date of Patent: *Sep. 15, 2020

(54) APPLICATOR

(71) Applicant: Debi Byrnes, North Hollywood, CA (US)

(72) Inventors: Debi Byrnes, North Hollywood, CA (US); Eric Paul Rose, Tarzana, CA (US)

(73) Assignee: Debi Byrnes, North Hollywood, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/453,386

(22) Filed: Jun. 26, 2019

(65) Prior Publication Data
US 2019/0313767 A1    Oct. 17, 2019

Related U.S. Application Data

(63) Continuation of application No. 15/485,445, filed on Apr. 12, 2017, now Pat. No. 10,368,625.

(60) Provisional application No. 62/497,051, filed on Nov. 8, 2016.

(51) Int. Cl.
| | |
|---|---|
| *A45D 34/04* | (2006.01) |
| *A45D 40/02* | (2006.01) |
| *A45D 40/26* | (2006.01) |
| *A61K 8/02* | (2006.01) |

(52) U.S. Cl.
CPC ............ *A45D 34/04* (2013.01); *A45D 40/26* (2013.01); *A61K 8/0208* (2013.01); *A45D 2200/1018* (2013.01)

(58) Field of Classification Search
CPC .................. A45D 34/04; A45D 40/26; A45D 2200/1018; A45D 34/00; A45D 40/00; A45D 2200/05; A45D 2200/10; A46B 50/02; A46B 5/04; A61K 8/0208; A61K 8/0204

See application file for complete search history.

(56) References Cited

U.S. PATENT DOCUMENTS

| | | |
|---|---|---|
| 2,686,325 A | 8/1954 | Silver |
| 3,806,260 A | 4/1974 | Miller |
| 3,955,233 A | 5/1976 | Nakamura |
| 4,111,567 A | 9/1978 | Berghahn et al. |
| 4,483,356 A | 11/1984 | Kales |
| 5,169,251 A | 12/1992 | Davis |
| 5,199,808 A | 4/1993 | Gueret |
| 5,240,339 A | 8/1993 | DeForest et al. |
| 5,772,347 A | 6/1998 | Gueret |
| 5,853,012 A | 12/1998 | Burns et al. |
| 5,931,591 A | 8/1999 | McCracken |

(Continued)

*Primary Examiner* — David J Walczak
(74) *Attorney, Agent, or Firm* — Jason P. Webb; Pearson Butler

(57) ABSTRACT

An applicator for applying creams, lotions, medicine, etc. to the body of a user. There is a sleeve coupled to a textured platform and/or reservoir. The sleeve is shaped and sized to friction fit to a pair of adjacent fingertips of a user and thereby to allow the user to beneficially apply, by fingertip control, fluid/cream/powder/etc. products. The textured platform includes an indented front portion, a reservoir, that is coupled to and/or integral to the sleeve such that when the sleeve is disposed over a pair of fingers, the indented front portion extends forward from the pads of the fingertips. There is also a tab.

20 Claims, 6 Drawing Sheets

(56) References Cited

U.S. PATENT DOCUMENTS

| | | |
|---|---|---|
| 6,214,362 B1 | 4/2001 | Page |
| 6,334,727 B1 | 1/2002 | Gueret |
| 6,415,470 B1 | 7/2002 | Ramrattan |
| 6,493,898 B1 | 12/2002 | Woods et al. |
| 7,108,440 B1 | 9/2006 | Gruenbacher et al. |
| 7,731,701 B2 | 6/2010 | Simon et al. |
| 7,811,021 B2 | 10/2010 | Gueret |
| 2002/0071708 A1 | 6/2002 | Fontanet et al. |
| 2006/0178067 A1 | 8/2006 | Mangold et al. |
| 2009/0317164 A1 | 12/2009 | Fukumoto et al. |
| 2012/0114408 A1 | 5/2012 | Limongi et al. |
| 2013/0058699 A1 | 3/2013 | Bollinger |
| 2013/0245687 A1 | 9/2013 | Bachmann |
| 2014/0250565 A1 | 9/2014 | Willows et al. |

APPLICATOR

CROSS-REFERENCE TO RELATED APPLICATIONS

This application is a Continuation Application of, under 35 U.S.C. § 120, and claims priority to, under 35 U.S.C. § 120, U.S. Pat. No. 10,386,625 entitled APPLICATOR, by Debi Byrnes et al., filed on Apr. 12, 2017. This invention claims priority therethrough, under 35 U.S.C. § 120, to the U.S. Provisional Patent Application No. 62/497,051 to Debi Byrnes filed et al on 8 Nov. 2016, which is incorporated by reference herein in its entirety.

FIELD OF THE INVENTION

The present invention relates to applicators, specifically to hand-held applicators of cosmetics, medicines, and related materials.

DESCRIPTION OF THE RELATED ART

Various creams, balms, powders, ointments, unguents and the like have been applied for centuries to the human body/hair/face for various purposes, including but not limited to as cosmetics, medicines, for religious purposes, and the like. Sometimes the method and manner of application is important. Variations in application may interfere with the benefits expected from the materials. Further, various materials may be more or less difficult to apply, to apply consistently, to apply safely, etc.

Accordingly, various devices and techniques for applying materials have been developed. Cotton balls/pads is an example of such a development. Cotton pads are generally pads made of cotton which are often used for medical or cosmetic purposes. For medical purposes, cotton pads are sometimes used to stop or prevent bleeding from minor punctures such as injections or venipuncture. They may be secured in place with tape. Cotton pads are also sometimes used in the application and the removal of makeup. Cotton pads are generally soft enough that they can also be used to clean babies. Despite their name, most modern cotton balls and pads are not made out of cotton at all but are instead made out of cheaper, bleached synthetic fibers such as polyester and nylon. In the United States, these products are frequently prominently labeled as "cotton balls."

In another example, brushes, sponges, dabbers/dabbing pads, gloves, and swabs are often used to apply materials to surfaces. Such brushes/pads are often used to apply blush, foundation, concealer, powder, etc. and for buffing finished applications. Similarly, such tools may be used medicinally to apply antiseptic, topical ointments, medicines to be absorbed through the skin, and the like. Often an applicator tool is limited in use to one material, as after use some of that material remains on/in the applicator until/unless cleaned. It is generally important to not mix materials and to be precise with regard to application.

Some improvements have been made in the field. Examples of references related to the present invention are described below in their own words, and the supporting teachings of each reference are incorporated by reference herein:

U.S. Pat. No. 5,169,251 issued to Davis, discloses a thin-walled protective glove having a self-contained palmar receptacle for storing various materials to be dispensed from the receptacle in response to the wearer's compressing or otherwise agitating the receptacle. The receptacle displays tributary conduits extending along the glove fingers to the fingertips and such conduits may have distal terminations through which materials are supplied to and dispensed from the receptacle. The receptacle and conduits may have perforations covered with sealing strips which are selectively removable to permit dispensing of stored material therethrough.

U.S. Pat. No. 5,240,339 issued to DeForest et al., discloses a body lotion applicator with an extended applicator head for reaching the back and other portions of the body that are difficult to reach. An elongate arm serves as a handle and conduit for conducting body lotions from a conventional bottle to the applicator head. The applicator head includes a face plate and porous sponge affixed thereto by a retaining ring. The sponge preferably consists of an outer layer of a small cell, open-cell foam and an inner body of a large cell, open-cell foam. The sponge is detachable from the head and is replaceable with a coarse-celled exfoliative sponge or similar sponge assembly.

U.S. Pat. No. 6,214,362 issued to Page, discloses a multi-functional cosmetic pad for either absorbing low tension substances from the skin or applying and smoothing new-makeup, comprising a porous low energy surface and crease resisting features for preventing the formation of creases, folds, or kinks when the surface is rubbed over the skin. A cosmetic pad in accordance with a preferred embodiment of the invention comprises a soft, conformable, and porous polytetraftuoroethylene membrane layered over a flexible backing. Flaps cutout from a top portion of the backing form a retractable handle for easily gripping and manipulating the cosmetic pad.

U.S. Pat. No. 7,108,440 issued to Gruenbacher et al., discloses an applicator for distributing a substance onto a target surface, said applicator including a first side having a first internal surface and a first external surface, a second side having a second internal surface and a second external surface and a flexible film dosing reservoir containing a product. The flexible film dosing reservoir is disposed between said first external surface of said first side and said second internal surface of said second side, said product adapted to be release [sic] via application of pressure to said reservoir.

U.S. Patent Application Publication No. 20060178067, by Mangold et al., discloses a disk or pad-shaped fiber composite article for the care and cleaning of human skin, comprising a non-woven fiber layer which forms one surface of the article and a thermoplastic film layer forming another surface thereof. The disk is characterised in that in order to form a more versatile fiber composite article, the thermoplastic film layer has a porous structure for receiving fatty components of human skin.

U.S. Patent Application Publication No. 20090317164 by Fukumoto et al., discloses an applicator of application substances, which can be repeatedly used and can be mounted on various containers, is provided. An applicator comprising: an application surface to be in contact with a target application surface and a support surface to be in contact with a finger being formed as integrated front and back surfaces; a mounting port matching an opening of an application substance container for housing an application substance; a discharge port being opened in the application surface; and a flow path guiding the application substance from the mounting port to the discharge port, penetrating between the application surface and the support surface.

The inventions and processes heretofore known suffer from a number of disadvantages Which include not being safe for fingers, wasting product, being difficult in product application, being slow in product application, absorbing product, failing to prevent finger irritation due to product exposure, failing to prevent accidental dosing due to product exposure to fingers, not being reusable, failing to reduce irritation, not being accurate in application, failing to provide controlled application and dosage of product, failing to allow a user to apply products that are less viscous, failing to prevent the product from sliding off the applicator, failing to provide a natural application style as opposed to a handle or grip, protecting the fingers from unwanted odors, failing to provide a consistent application surface, and failing to allow the user to apply product by feel.

What is needed is an applicator that solves one or more of the problems described herein and/or one or more problems that may come to the attention of one skilled in the art upon becoming familiar with this specification.

SUMMARY OF THE INVENTION

The present invention has been developed in response to the present state of the art, and in particular, in response to the problems and needs in the art that have not yet been fully solved by currently available applicators. Accordingly, the present invention has been developed to provide an applicator for manual application of materials to a user.

In one non-limiting embodiment, there is an applicator, consisting of a sleeve that may be shaped to receive a pair of adjacent fingers of a user and/or elastically couple thereabout, the sleeve may be including a thicker front-region that may have a tab that may protrude from an open end of the sleeve; and a reservoir that may be disposed in a front-region of the sleeve.

The sleeve may include a closed end that may be opposite the open end and/or the reservoir and may include surface textures that may be shaped to collect material.

The reservoir may be a concave reservoir that may consist of a single cavity that may have a depth that may be less than $1/20^{th}$ of its circumference. The concave reservoir may include a beveled edge that may form a boundary between a bottom of the reservoir and an exterior surface of front region of the sleeve. The beveled edge may have an interior angle with respect to the bottom of the reservoir greater than 90 degrees. The concave reservoir may include a sharp edge that may form a boundary between a bottom of the reservoir and an exterior surface of the front region of the sleeve. The beveled edge may have an interior angle that may be equal to or less than 90 degrees.

It may be that applicator consists of a single molded piece of a single material-type. It may be that the applicator consists of a non-absorbent, elastic, and water impervious material. It may be that the applicator consists of one or more materials selected from the group of materials consisting of: rubber, silicone, and polyethylene.

In another non-limiting embodiment, there is an applicator for manual application of non-solid personal care products to a person, comprising a sleeve shaped to receive a pair of adjacent fingers of a user and elastically couple thereabout, the sleeve including a thicker front-region; and a textured reservoir disposed in a front-region of the sleeve.

The sleeve may include an open end and/or a closed end that may be opposite the open end.

It may be that the applicator is a single molded piece of a material that is non-absorbent, elastic, and/or water impervious material.

There may be a tab that may protrude from an open end of the sleeve. The tab may include one or more winglets at each side thereof that may extend backwardly from the tab.

The textured reservoir may be a concave reservoir that may include a beveled edge that may form a boundary between a bottom of the reservoir and an exterior surface of front region of the sleeve. The beveled edge may have an interior angle with respect to the bottom of the reservoir greater than 90 degrees. It may be that the textured reservoir is a concave reservoir that may consist of a single cavity that may have a depth less than $1/20^{th}$ of its circumference.

In still yet another non-limiting embodiment, there is an applicator for manual application of non-solid personal care products to a person, consisting essentially of a sleeve that may be shaped to receive a pair of adjacent fingers of a user and/or elastically couple thereabout, the sleeve may include a thicker front-region that may have a tab that may extending outwardly from an open end of the sleeve; and/or a concave reservoir that may be disposed in a front-region of the sleeve.

It may be that the applicator is a single molded piece of a material that is non-absorbent, elastic, and/or water impervious material.

It may be that the concave reservoir consists of a single cavity that may have a depth less than $1/20^{th}$ of its circumference and/or that the single cavity has a beveled edge forming a boundary between a bottom of the reservoir and an exterior surface of front region of the sleeve. It may be that the beveled edge having an interior angle with respect to the bottom of the reservoir that may be greater than 90 degrees. It may be that the concave reservoir includes a first cavity having a second cavity disposed thereinside. It may be that the concave reservoir is circular.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention can be practiced without one or more of the specific features or advantages of a particular embodiment. In other instances, additional features and advantages may be recognized in certain embodiments that may not be present in all embodiments of the invention.

These features and advantages of the present invention will become more fully apparent from the following description and appended claims, or may be learned by the practice of the invention as set forth hereinafter.

BRIEF DESCRIPTION OF THE DRAWINGS

In order for the advantages of the invention to be readily understood, a more particular description of the invention briefly described above will be rendered by reference to specific embodiments that are illustrated in the appended drawing(s). It is noted that the drawings of the invention are not to scale. The drawings are mere schematics representations, not intended to portray specific parameters of the invention. Understanding that these drawing(s) depict only typical embodiments of the invention and are not, therefore, to be considered to be limiting its scope, the invention will be described and explained with additional specificity and detail through the use of the accompanying drawing(s), in which.

DETAILED DESCRIPTION OF THE INVENTION

Figure 1:
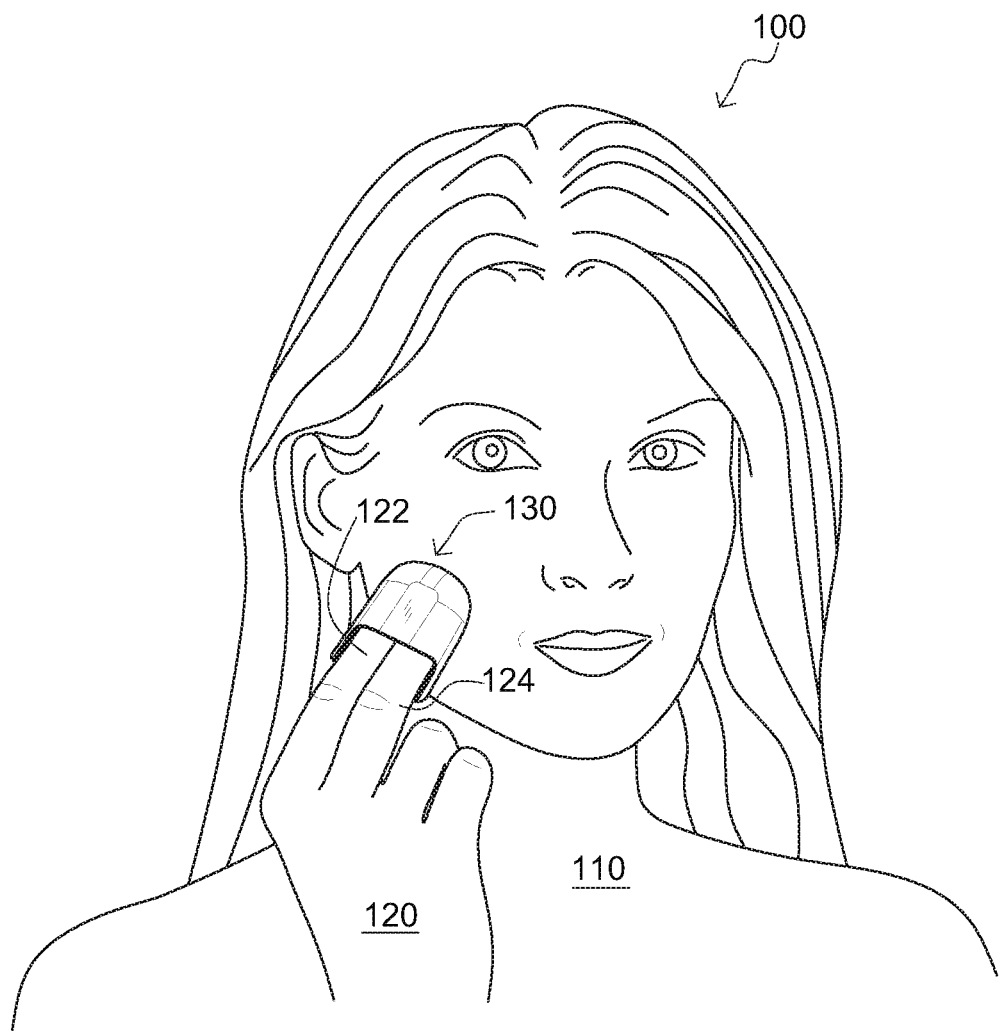
FIG. 1 illustrates an applicator in operation on a user's fingers applying product to a user's face, according to one embodiment of the invention.

For the purposes of promoting an understanding of the principles of the invention, reference will now be made to the exemplary embodiments illustrated in the drawing(s), and specific language will be used to describe the same. It will nevertheless be understood that no limitation of the scope of the invention is thereby intended. Any alterations and further modifications of the inventive features illustrated herein, and any additional applications of the principles of the invention as illustrated herein, which would occur to one skilled in the relevant art and having possession of this disclosure, are to be considered within the scope of the invention.

Reference throughout this specification to an "embodiment," an "example" or similar language means that a particular feature, structure, characteristic, or combinations thereof described in connection with the embodiment is included in at least one embodiment of the present invention. Thus, appearances of the phrases an "embodiment," an "example," and similar language throughout this specification may, but do not necessarily, all refer to the same embodiment, to different embodiments, or to one or more of the figures. Additionally, reference to the wording "embodiment," "example" or the like, for two or more features, elements, etc. does not mean that the features are necessarily related, dissimilar, the same, etc.

Each statement of an embodiment, or example, is to be considered independent of any other statement of an embodiment despite any use of similar or identical language characterizing each embodiment. Therefore, where one embodiment is identified as "another embodiment," the identified embodiment is independent of any other embodiments characterized by the language "another embodiment." The features, functions, and the like described herein are considered to be able to be combined in whole or in part one with another as the claims and/or art may direct, either directly or indirectly, implicitly or explicitly.

As used herein, "comprising," "including," "containing," "is," "are," "characterized by," and grammatical equivalents thereof are inclusive or open-ended terms that do not exclude additional unrecited elements or method steps. "Comprising" is to be interpreted as including the more restrictive terms "consisting of" and "consisting essentially of."

FIG. 1 illustrates an applicator in operation 100 on a user's fingers 122, 124 applying product to a user's face, according to one embodiment of the invention. There is shown a person 110 with an applicator 130 disposed on two fingers 122, 124 of a hand 120 of the user.

The illustrated fingers 122, 124 are inserted within a cavity of the applicator such that the applicator friction fits about the fingers. Having two fingers disposed within a friction fitting cavity of the applicator allows for enhanced control and finer manipulation of the applicator. Further, it allows the applicator to act as an extension of the fingers of the user, thereby making control thereof more natural and easier to learn, especially for those with coordination difficulties or disabilities.

The illustrated applicator is of a single piece of uniform material that is water impervious, non-absorbent, and flexible, thus friction fitting to the fingers of the user, while not absorbing the materials to be applied to/by the user. Such a material may be of a rubber, silicone, and/or polymer material (e.g. polyethylene), thereby providing a solid but flexible application surface and interface with the fingers of the user that does not absorb materials collected thereon.

In operation, the user gathers material to be applied to the user onto a front region of the applicator and then turns that same front region to the area where the material should be applied. The user then brushes/slides the front region of the applicator against the surface where the material is to be applied to smear/apply the material at that location. The user may use the applicator to continue to apply the material in order to spread out the same and/or provide a desired application, such as but not limited to producing an even coating of material at a particular location.

Figure 2:
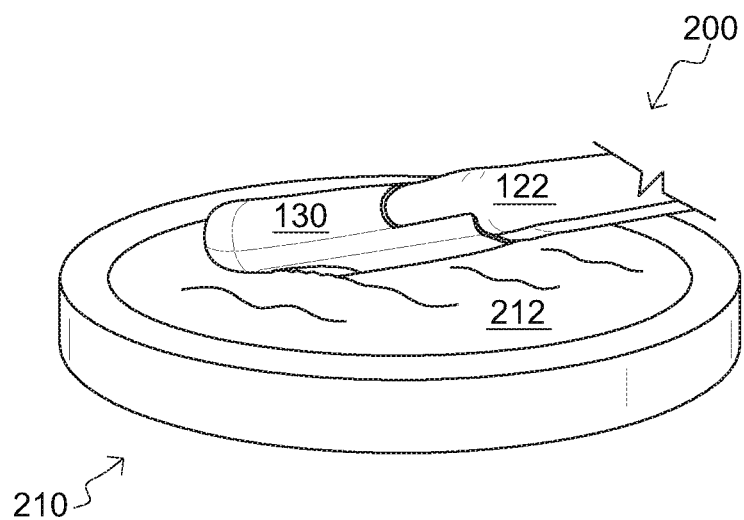
FIG. 2 illustrates an applicator in operation on a user's fingers gathering product from a product dish, according to one embodiment of the invention.

FIG. 2 illustrates an applicator 130 in operation 200 on a user's fingers 122 (124 not labeled) gathering product 212 from a product dish 210, according to one embodiment of the invention.

The illustrated product dish 210 includes a product/material 212 to be applied, which the user gathers into a reservoir and/or textured platform on a front face of the applicator 130 by sliding the front face of the applicator across a top surface of the product 212 in a manner that allows such material to gather into/about the reservoir. Such materials are generally sticky/tacky creams, lotions, etc. and therefore will adhere to the reservoir when so contacted by the applicator.

The materials to be applied may vary according to the needs of the user, Such may include one or more cosmetics and/or medications or even other materials such as but not limited to fluid applications used in spiritual or religious ceremonies. Non-limiting examples of cosmetics that may be so applied include: foundation, blush, powder, creams, gloss, primer, stain, concealer, blemish balm, contour powders/creams, highlights, bronzer, adhesives for application of cosmetics, waxes, gels, polishes, and setting materials. Non-limiting examples of medications that may be so applied include: balms, ointments, acne medication, burn creams, moisturizers, antiseptic creams/lotions/gels, skin absorbent medications (e.g. steroids, hormones), soaps/detergents, antibiotics, antifungal treatments, rash ointments, cold sore ointments, wart/mole removing creams, and skin rejuvenation treatments. Other materials that may be applied include but are not limited to essential oils, ground/mashed herbs, mineral compositions, inks/dyes, ashes, and waxes. Of note, some of the materials that may be applied may be materials where, if applied using naked fingers, may cause difficulties or create issues due to unintended medical dosing through absorption into the skin of the fingers, may waste expensive materials (e.g. expensive essential oils), or may otherwise cause problems if applied just with the fingers. Similar problems may occur if using cotton balls or other absorbent materials.

Figure 3:
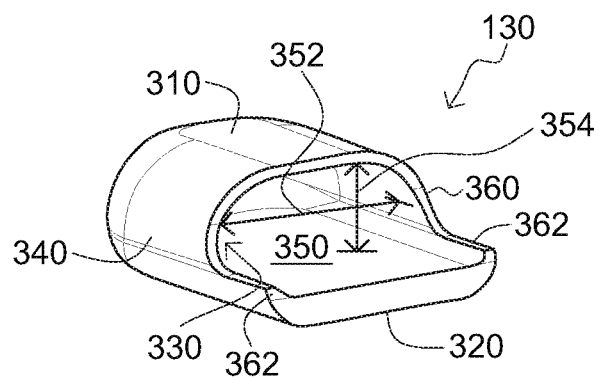
FIG. 3 illustrates a perspective rear-bottom view of an applicator, according to one embodiment of the invention.
Figure 4:
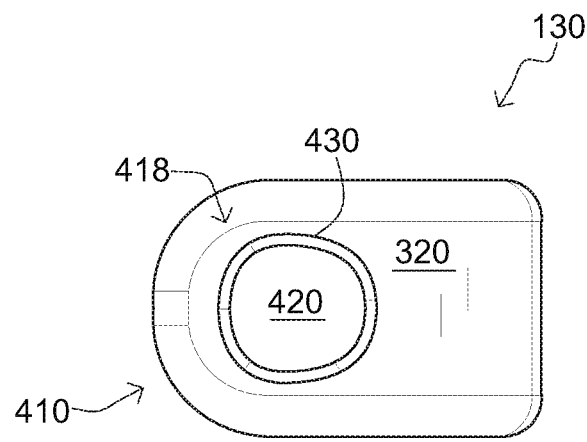
FIG. 4 illustrates a front plan view of an applicator, according to one embodiment of the invention.
Figure 5:
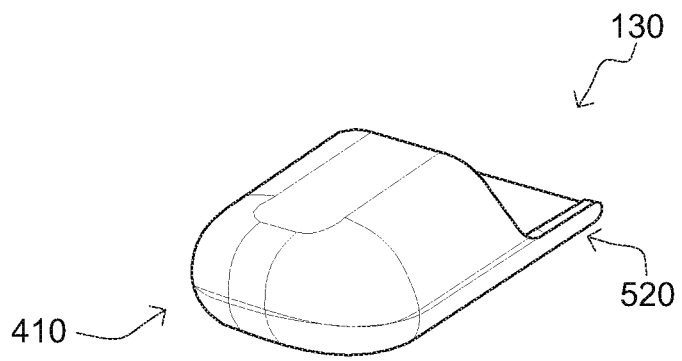
FIG. 5 illustrates a top-rear perspective view of an applicator, according to one embodiment of the invention.

FIGS. 3-5 illustrate various views of an applicator, according to one embodiment of the invention. There is shown an applicator 130 with a sleeve 36 having a front region 320 (See FIG. 4, front view) and a rear region 310 (may also be called a planar back region) coupled by side regions 340 and bounded on a closed end by a top region 410, whereby forming a cavity 330 within which a user may insert two adjacent fingers, thereby coupling the applicator to the user (i.e. friction fit), wherein a base of the cavity 330 is formed by the closed end/top region 410 opposite a mouth of the cavity 330. The front region 320 includes a tab 520 and a reservoir 418 having a reservoir bottom 420 circumscribed by a reservoir edge 430. The illustrated reservoir bottom is flat. The illustrated applicator allows a user to apply materials to themselves in an even, consistent manner, with ease, without losing material to absorption within the applicator and without exposing the material to the fingers of the user.

The illustrated sleeve 36 is a single molded body of material having a front region 320 coupled to a rear region 310 by side regions 340 and a top region 410. The illustrated front region 320 is thicker than the illustrated side 340 and rear regions 310 The sleeve is shaped and configured to receive a pair of fingers of a user and thereby couple to the hand of the user and allow the user to manipulate and control the applicator by fingertip actuation. This provides a high degree of easy, natural control while providing a consistently shaped application surface having a reservoir within which material may be stored during operation.

The illustrated reservoir 418 is a shallow cavity inset into the front region/face of the applicator. The reservoir is bounded by a reservoir edge 430 and the shape of that edge determines some of the operation thereof. Wherein the edge is a gradual curved transition, without any right angles or acute angles, between the planar front surface 320 and a planar reservoir bottom 420, the reservoir will easily dispense material from the reservoir, thereby tending to apply thicker layers and needing to be replenished more often than if the reservoir edge has right angles or acute angles.

The illustrated cavity 330 is of a height 354 and a width 352 and includes a base 350 against which a user presses their fingers during operation. The height may be less than the average height of a human finger knuckle so as to friction fit thereto. The width may be less than an average width of two human finger knuckles so as to friction fit thereto. It may be that the width is about twice the height. It may be that the height is less than 2.0 cm, 1.9 cm, 1.8 cm, 1.7 cm, 1.6 cm, 1.5 cm, 1.4 cm, 1.3 cm, 1.1 cm, and/or 1.0 cm. It may be that a width may be less than about 4.0 cm, 3.8 cm, 3.6 cm, 3.4 cm, 3.2 cm, 3.0 cm, 2.8 cm, 2.6 cm, 2.4 cm, 2.2 cm, and/or 2.0 cm. It may be that a ratio of the width to the height may be between one or more of 1.6, 1.7, 1.8, 1.9, 2.0. 2.1, 2.2, 2.3, and 2.4.

The illustrated applicator consists of a sleeve and a reservoir.

The illustrated sleeve is shaped to receive a pair of adjacent fingers of a user and elastically couple thereabout. The sleeve includes a thicker front-region having a tab protruding from an open end (mouth) of the sleeve. The sleeve includes a closed end opposite the open end and the reservoir includes surface textures shaped to collect material. The illustrated open end is an oblong mouth, which is the only opening on the illustrated sleeve.

Figure 7:
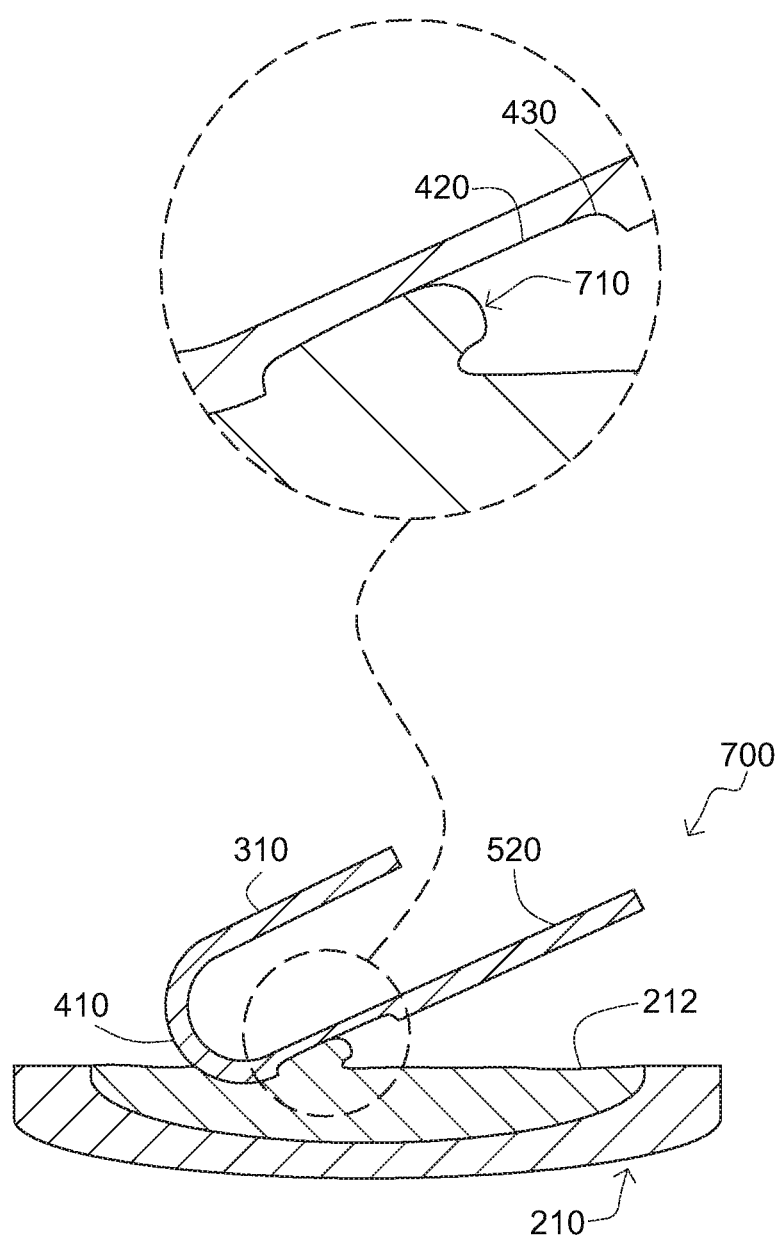
FIG. 7 is a cross-sectional view of an applicator collecting material from a dish, according to one embodiment of the invention, showing a close-up view thereof.

The illustrated reservoir is disposed in a front-region of the sleeve. The illustrated reservoir is a concave reservoir that is circular. The illustrated reservoir is a concave reservoir that consists of a single cavity. It may be that the cavity has a depth less than $1/30^{th}$; $1/20^{th}$; $1/15^{th}$; $1/10^{th}$; $1/5^{th}$; and/or $1/3^{rd}$ of its circumference, and/or is less than 0.05 mm, 1 mm, 2 mm, and/or 3 mm deep, as compared to the planar front surface. The illustrated concave reservoir includes a beveled edge forming a boundary between a bottom of the reservoir and an exterior surface of front region of the sleeve, the beveled edge 430 as illustrated in FIG. 7 has an interior angle with respect to the bottom of the reservoir greater than 90 degrees. In an alternative embodiment, the concave reservoir includes a sharp edge forming a boundary between a bottom of the reservoir and an exterior surface of the front region of the sleeve, the beveled edge having an interior angle equal to or less than 90 degrees. Such would make it easier to collect material quickly and would tend to reduce a thickness of application on the surface where the material is being applied.

In one non-limiting embodiment, there is a sleeve coupled to a textured platform and/or reservoir. The sleeve is shaped and sized to friction fit to a pair of adjacent fingertips of a user and thereby to allow the user to beneficially apply, by fingertip control, fluid/cream/powder/etc. products. The textured platform may include an indented front portion (reservoir) that is coupled to and/or integral to the sleeve such that when the sleeve is disposed over a pair of fingers, the indented front portion extends forward from the pads of the fingertips.

Figure 11:
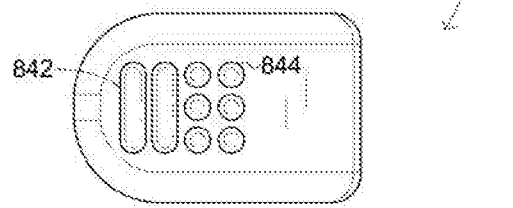

Such a sleeve may take various forms, including but not limited to being a strap, clip, elastic band, wrap, sock, and/or a friction-fitting wing between fingertips. The sleeves primary function is to couple the textured platform to a front portion of the fingertips of the user. The illustrated front region 320 is a textured platform. Such a textured platform may take various forms, including but not limited to having variously shaped indented portions (See FIG. 8-11 for non-limiting examples), could include textures with no indentation, an indentation could be a ridge instead of a valley (e.g. item 842 of FIG. 11). It may be that the front region/platform is not thicker than the surrounding material of the sleeve. The sleeve and/or platform may be of a material that is non-silicone but still non-absorbent and flexible. The front region/platform may be segmented instead of a single planer unit.

Figure 8:
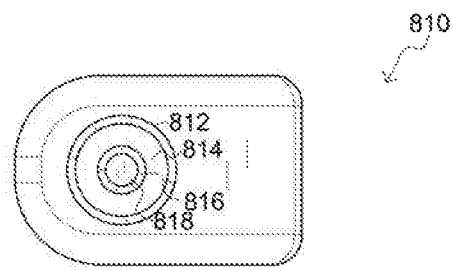
FIGS. 8-11 show a plurality of front plan views of applicators having varying textured reservoirs.
Figure 9:
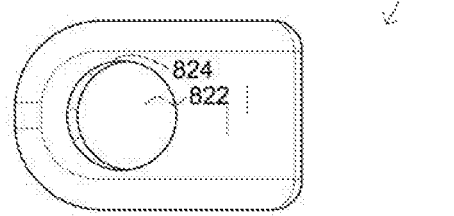
Figure 10:
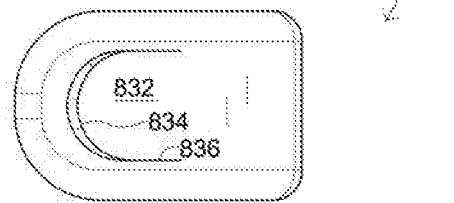

It may be that the concave reservoir includes a first cavity having a second cavity disposed thereinside (See FIG. 8).

There is shown an applicator for manual application of non-solid (e.g., powder, cream, lotion, liquid, foam) personal care products to a person, comprising a sleeve shaped to receive a pair of adjacent fingers of a user and elastically couple thereabout, the sleeve including a thicker front-region; and a textured reservoir disposed in a front-region of the sleeve. The illustrated sleeve includes an open end and a closed end opposite the open end. There is shown a tab protruding from an open end of the sleeve. The tab includes winglets 362 at each side thereof that extend backwardly from the tab.

There may be an applicator for manual application of non-solid personal care products to a person, consisting essentially of a sleeve and a concave reservoir. Such an applicator would be lacking in additional components/structures that would detract from the following benefits/purposes of such an applicator: inexpensive, durable, easy to use, easy to control, consistent in application of materials, easy to gather materials on a front region thereof, protecting the fingers of the user, not absorbing materials, providing a natural style of control, and easy to clean.

There may be an applicator for skin care, medicinal and/or cosmeceutical skin care products. Such may be different from other applicators in that it does not absorb the product and a user's fingers do not come in contact with the product being applied. The applicator may be water-impervious and pliable. Generally, the pointer and adjacent middle finger of the user are inserted into the applicator. Such protects ones fingers from the ingredients. Such may be a molded piece of material (e.g. silicone, rubber, polyethylene) that has an opening for two fingers to fit in. Such may be thicker on the bottom and may have a texture and/or a small indented area for the product to be placed on during operation.

Figure 6:
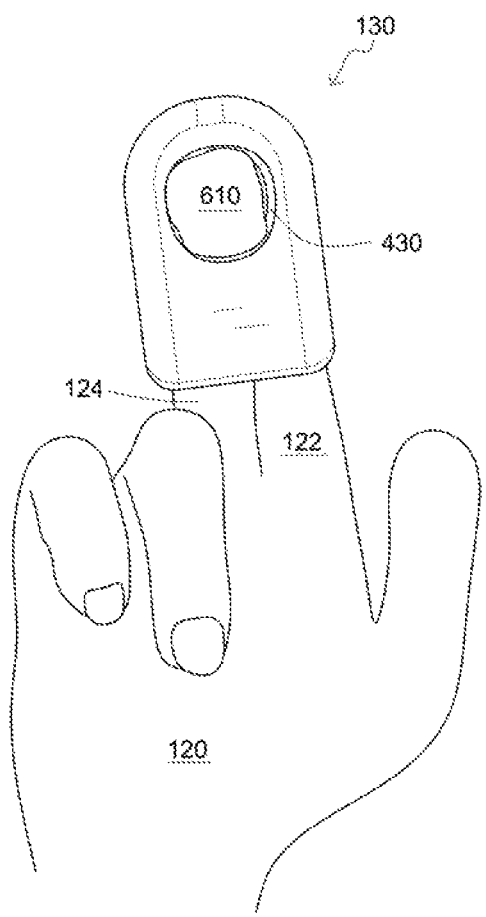
FIG. 6 is a front view of an applicator disposed on the fingers of a user with product disposed within the reservoir of the applicator, according to one embodiment of the invention.

FIG. 6 is a front view of an applicator disposed on the fingers of a user with product disposed within the reservoir of the applicator, according to one embodiment of the invention. The illustrated applicator 130 is coupled to a hand 120 of a user at the fingers 122, 124. The applicator 130 has a body of material 610 stuck thereto within a reservoir having a reservoir edge 430. The illustrated applicator is primed to be used to apply such material 610 as desired, e.g. to the face of the user.

FIG. 7 is a cross-sectional view of an applicator collecting 700 material from a dish, according to one embodiment of the invention, showing a close-up view thereof. FIG. 7 omits the fingers of the user to simplify the illustration and focus on the structure of the applicator. The presence of the fingers of the user within the applicator is implied.

The illustrated applicator in the midst of collecting material 212 from a dish 210 of such material. While applicant shows such a dish in the figures, it is understood that an applicator may be loaded with materials in other ways, including but not limited to wiping from another surface/applicator, squeezing such material out of a tube, dabbing from a surface, applying with a brush/swab, and the like and combinations thereof. The illustrated reservoir, as the applicator is drawn backwards across the surface of the material 212, catches the material within the reservoir, according to the structural characteristics of the edge 430 in combination with the tackiness/stickiness of the material and thereby lifts a body of material 710 into the reservoir.

FIG. 8-11 show a plurality of front plan views of applicators having varying textured reservoirs. There is shown four applicators 810, 820, 830, and 846, respectively from top to bottom, each having different textured platforms (i.e. front regions). These may be identified as the first 810, second 820, third 830, and fourth 846 illustrated embodiments of FIGS. 8-11. These are non-limiting embodiments that illustrate a variety of textured platform configurations that may be present in one or more embodiments of the invention.

The first shows a double bottomed reservoir. This reservoir has a first edge 812 that leads to a first reservoir bottom 814 that includes a second concentric edge 816 that leads to a second reservoir bottom 818 that is deeper than the first bottom with respect to the planar front face.

The second shows a beveled edge 824 having an angle with respect to the bottom 822 near a top of the applicator that is greater than 90 degrees while having a right-angle edge opposite the beveled edge 824.

The third shows a beveled edge 834 having an angle with respect to the bottom 832 near a top of the applicator that is greater than 90 degrees while having a sloped bottom that gradually becomes flush with the planar front face. Accordingly the illustrated side wall 836 of the reservoir is deeper/higher at the deep end and gradually decreases to nothing going away from the deep end.

The fourth shows an embodiment with no cavities, but instead includes a plurality of protrusions. There is a first set of protrusions 842 near a top portion of the front face that are pill-shaped. There is a second set of protrusions 844 that includes an array of six bottom-shaped protrusions opposite the pill-shaped protrusions. Material may be gathered between the protrusions and then applied from that state.

It is understood that the above-described embodiments are only illustrative of the application of the principles of the present invention. The present invention may be embodied in other specific forms without departing from its spirit or essential characteristics. The described embodiment is to be considered in all respects only as illustrative and not restrictive. The scope of the invention is, therefore, indicated by the appended claims rather than by the foregoing description. All changes which come within the meaning and range of equivalency of the claims are to be embraced within their scope.

It is expected that there could be numerous variations of the design of this invention. An example is that the exterior shape of the applicator may be stylized, shaped, textured, and/or may include layers of decorative material and/or printing thereon, and/or otherwise decorated. Such may be suited to particular demographics (e.g. kids) and/or stylized to include licensed characters and/or branding.

Finally, it is envisioned that the components of the device may be constructed of a variety of materials, including but not limited to silicone, plastic, rubber, polyethylene, latex, polyisoprene (i.e. synthetic rubber), and nitrile.

Thus, while the present invention has been fully described above with particularity and detail in connection with what is presently deemed to be the most practical and preferred embodiment of the invention, it will be apparent to those of ordinary skill in the art that numerous modifications, including, but not limited to, variations in size, materials, shape, form, function and manner of operation, assembly and use may be made, without departing from the principles and concepts of the invention as set forth in the claims. Further, it is contemplated that an embodiment may be limited to consist of or to consist essentially of one or more of the features, functions, structures, methods described herein.

What is claimed is:

1. An applicator, consisting of:
   a. a sleeve shaped to receive a pair of adjacent fingers of a user and elastically couple thereabout, the sleeve including a thicker front-region having a tab protruding from an open end of the sleeve, wherein the sleeve includes a cavity having an oblong mouth with no other openings in the sleeve; and
   b. a reservoir disposed in the thicker front-region of the sleeve.

2. The applicator of claim 1, wherein the sleeve includes a closed end opposite the open end and the reservoir includes surface textures shaped to collect material.

3. The applicator of claim 1, wherein the reservoir is a concave reservoir that consists of a single cavity having a depth less than $\frac{1}{20}^{th}$ of its circumference.

4. The applicator of claim 3, wherein the concave reservoir includes a sharp edge forming a boundary between a bottom of the reservoir and an exterior surface of the front region of the sleeve, the sharp edge having an interior angle equal to or less than 90 degrees.

5. The applicator of claim 3, wherein the concave reservoir includes a beveled edge forming a boundary between a bottom of the reservoir and an exterior surface of the thicker front region of the sleeve, the beveled edge having an interior angle with respect to the bottom of the reservoir greater than 90 degrees.

6. The applicator of claim 1, wherein the applicator consists of a single molded piece of a single material-type.

7. The applicator of claim 1, wherein the applicator consists of a non-absorbent, elastic, and water impervious material.

8. The applicator of claim 1, wherein the applicator consists of one or more materials selected from the group of materials consisting of: rubber, silicone, and polyethylene.

9. An applicator for manual application of non-solid personal care products to a person, comprising:
   a. a sleeve shaped to receive a pair of adjacent fingers of a user and elastically couple thereabout, the sleeve including a planar front-region and a back region, wherein the planar front region is thicker than the back region along its entirety; and
   b. a reservoir disposed in the planar front region of the sleeve, the reservoir being a flat depression disposed within the planar front region.

10. The applicator of claim 9, wherein the sleeve includes an open end and a closed end opposite the open end.

11. The applicator of claim 10, wherein the applicator is a single molded piece of a material that is non-absorbent, elastic, and water impervious material.

12. The applicator of Claire 11, further comprising a tab protruding from an open end of the sleeve.

13. The applicator of claim 12, wherein the tab includes winglets at each side thereof that extend backwardly from the tab.

14. The applicator of claim 11, wherein the textured reservoir is a concave reservoir that includes a beveled edge forming a boundary between a bottom of the reservoir and an exterior surface of the thicker front region of the sleeve, the beveled edge having an interior angle with respect to the bottom of the reservoir greater than 90 degrees.

15. The applicator of claim 11, wherein the textured reservoir is a concave reservoir that consists of a single cavity having a depth less than $\frac{1}{20}^{th}$ of its circumference.

16. An applicator for manual application of non-solid personal care products to the face of a person, consisting essentially of:
   a. a sleeve having a cavity with a an oblong mouth and thereby shaped to receive a pair of adjacent fingers of a user and elastically couple thereabout, the sleeve including a front-region having a tab extending outwardly from an open end of the sleeve, wherein the front-region does not include any protrusions; and
   b. a concave reservoir having a flat bottom recessed into the front-region of the sleeve.

17. The applicator of claim 16, wherein the applicator is a single molded piece of a material that is non-absorbent, elastic, and water impervious material.

18. The applicator of claim 16, wherein the concave reservoir consists of a single cavity having a depth less than $\frac{1}{20}^{th}$ of its circumference and the single cavity has a beveled edge forming a boundary between a bottom of the reservoir and an exterior surface of the thicker front region of the sleeve, the beveled edge having an interior angle with respect to the bottom of the reservoir greater than 90 degrees.

19. The applicator of claim 16, wherein the concave reservoir includes a first cavity having a second cavity disposed thereinside.

20. The applicator of claim 16, wherein the concave reservoir is circular.

* * * * *